(12) United States Patent
Greskovich, Jr. et al.

(10) Patent No.: US 10,335,609 B2
(45) Date of Patent: Jul. 2, 2019

(54) MULTITUBE ESOPHAGEAL BRACHYTHERAPY CATHETER

(71) Applicant: THE CLEVELAND CLINIC FOUNDATION, Cleveland, OH (US)

(72) Inventors: John Greskovich, Jr., Shaker Hts., OH (US); Shengqiang Gao, Beachwood, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 497 days.

(21) Appl. No.: 14/847,927

(22) Filed: Sep. 8, 2015

(65) Prior Publication Data
US 2016/0051839 A1    Feb. 25, 2016

Related U.S. Application Data

(63) Continuation-in-part of application No. 14/198,793, filed on Mar. 6, 2014, now Pat. No. 9,764,158.
(Continued)

(51) Int. Cl.
*A61N 5/10*    (2006.01)

(52) U.S. Cl.
CPC .... *A61N 5/1002* (2013.01); *A61N 2005/1003* (2013.01); *A61N 2005/1004* (2013.01);
(Continued)

(58) Field of Classification Search
CPC .......... A61N 5/1001–1017; A61N 2005/1003; A61N 2005/1004; A61N 2005/1007;
(Continued)

(56) References Cited

U.S. PATENT DOCUMENTS

| 5,653,683 A | * | 8/1997 | D'Andrea | A61N 5/1014 600/2 |
| 5,782,740 A | * | 7/1998 | Schneiderman | A61M 25/104 600/1 |

(Continued)

FOREIGN PATENT DOCUMENTS

WO    0051136 A1    8/2000

OTHER PUBLICATIONS

Chinese Office Action corresponding to Chinese Patent Application No. 201480014260.2, dated Aug. 29, 2017, pp. 1-5.
(Continued)

*Primary Examiner* — Catherine B Kuhlman
(74) *Attorney, Agent, or Firm* — Tarolli, Sundheim, Covell & Tummino LLP

(57) ABSTRACT

A system for delivery of radiation to a target portion of a native tissue is provided. The system includes a catheter having a catheter body with a proximal portion, a distal portion, and a longitudinally oriented lumen therebetween. The system further includes an expansion device disposed about at least a portion of the catheter body and having an expanded configuration and a non-expanded configuration. The system also includes a plurality of tubes disposed about at least a portion of the expansion device. Each of the plurality of tubes is configured to selectively guide exposure of a radiation source to the target portion of the native tissue.

12 Claims, 15 Drawing Sheets

Related U.S. Application Data

(60) Provisional application No. 61/777,671, filed on Mar. 12, 2013.

(52) U.S. Cl.
CPC ............... *A61N 2005/1005* (2013.01); *A61N 2005/1018* (2013.01); *A61N 2005/1094* (2013.01)

(58) Field of Classification Search
CPC .... A61N 2005/1008; A61N 2005/1012; A61N 2005/1014–1018
See application file for complete search history.

(56) References Cited

U.S. PATENT DOCUMENTS

| | | | |
|---|---|---|---|
| 6,607,477 | B1 | 8/2003 | Longton et al. |
| 6,746,392 | B2 | 6/2004 | Stiger et al. |
| 8,137,256 | B2 | 3/2012 | Cutrer et al. |
| 8,226,539 | B2 | 7/2012 | Cutrer et al. |
| 2006/0100475 | A1* | 5/2006 | White ............... A61N 5/1015 600/3 |
| 2006/0100476 | A1 | 5/2006 | Biscotti |
| 2007/0106108 | A1 | 5/2007 | Hermann et al. |
| 2008/0221384 | A1 | 9/2008 | Chi Sing et al. |
| 2010/0048977 | A1 | 2/2010 | Sing et al. |
| 2012/0012120 | A1* | 1/2012 | Giffey ............... A61B 1/24 128/860 |
| 2012/0071705 | A1 | 3/2012 | Lubock et al. |

OTHER PUBLICATIONS

PCT International Search Report and Written Opinion for PCT/US2014/021011, dated Jun. 2, 2014, pp. 1-11.

Search Report for corresponding Chinese Appl. No. 201480014260.2, dated Dec. 26, 2016, pp. 1-2.

Office Action for corresponding Chinese Appl. No. 201480014260.2, dated Jan. 4, 2017, pp. 1-8.

EPO Examination Report for corresponding EP App. No. 14714855.5, dated Dec. 16, 2016, pp. 1-5.

\* cited by examiner

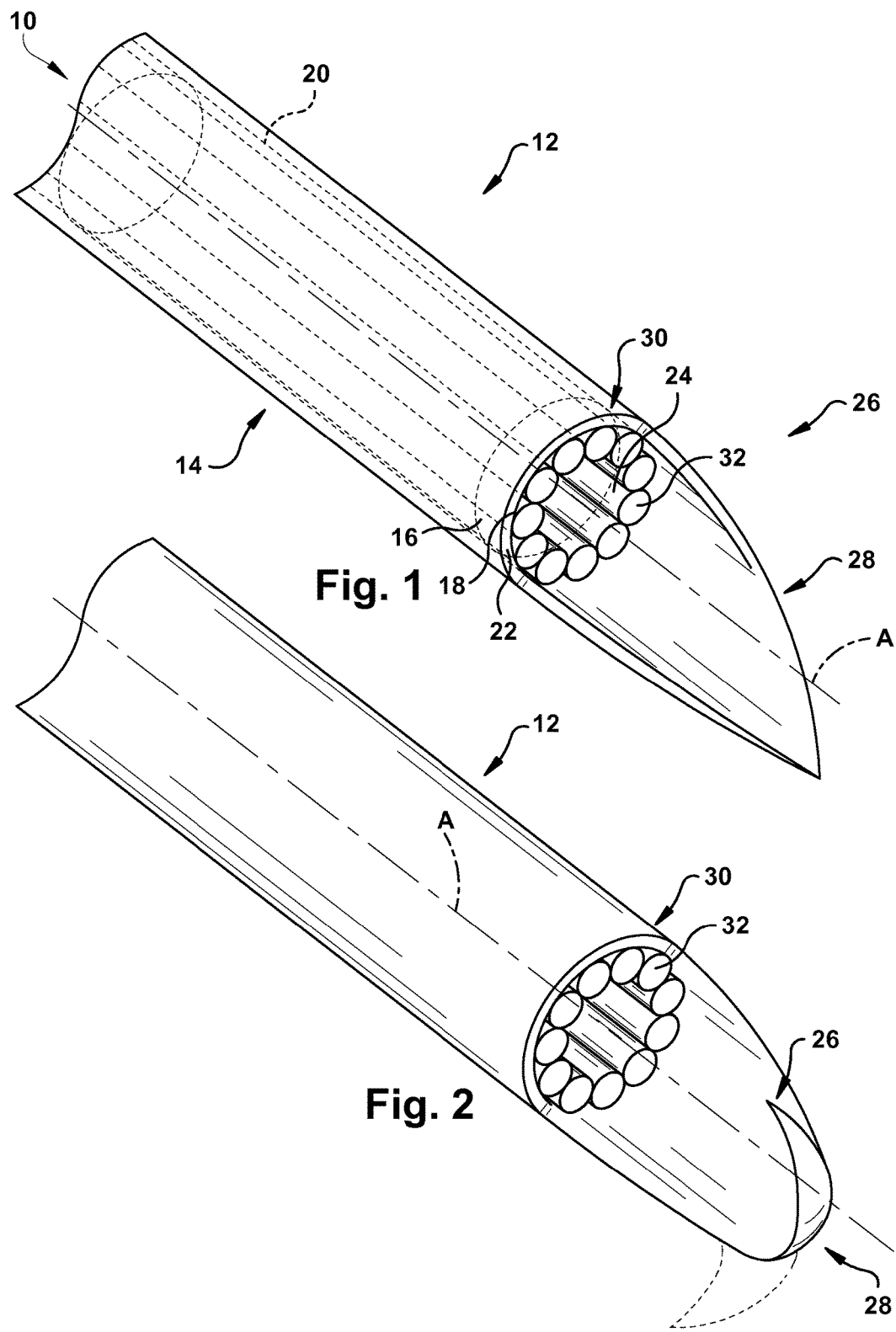

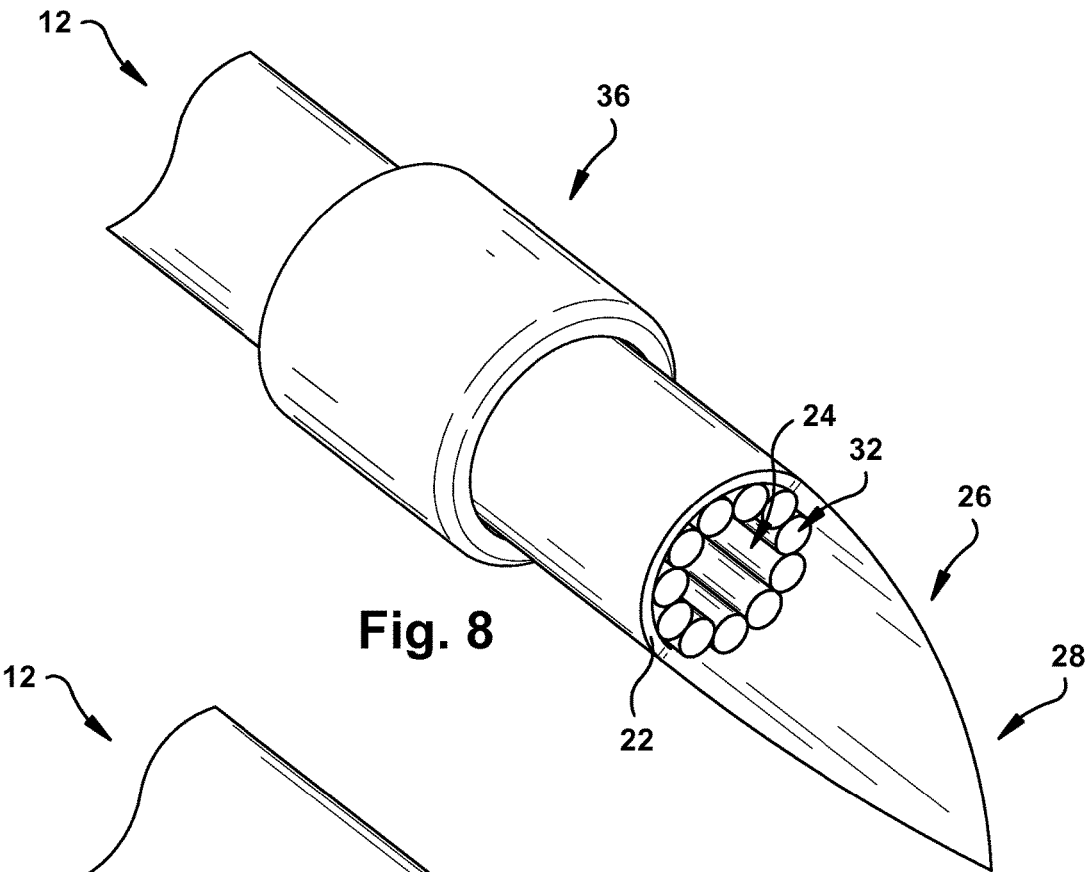
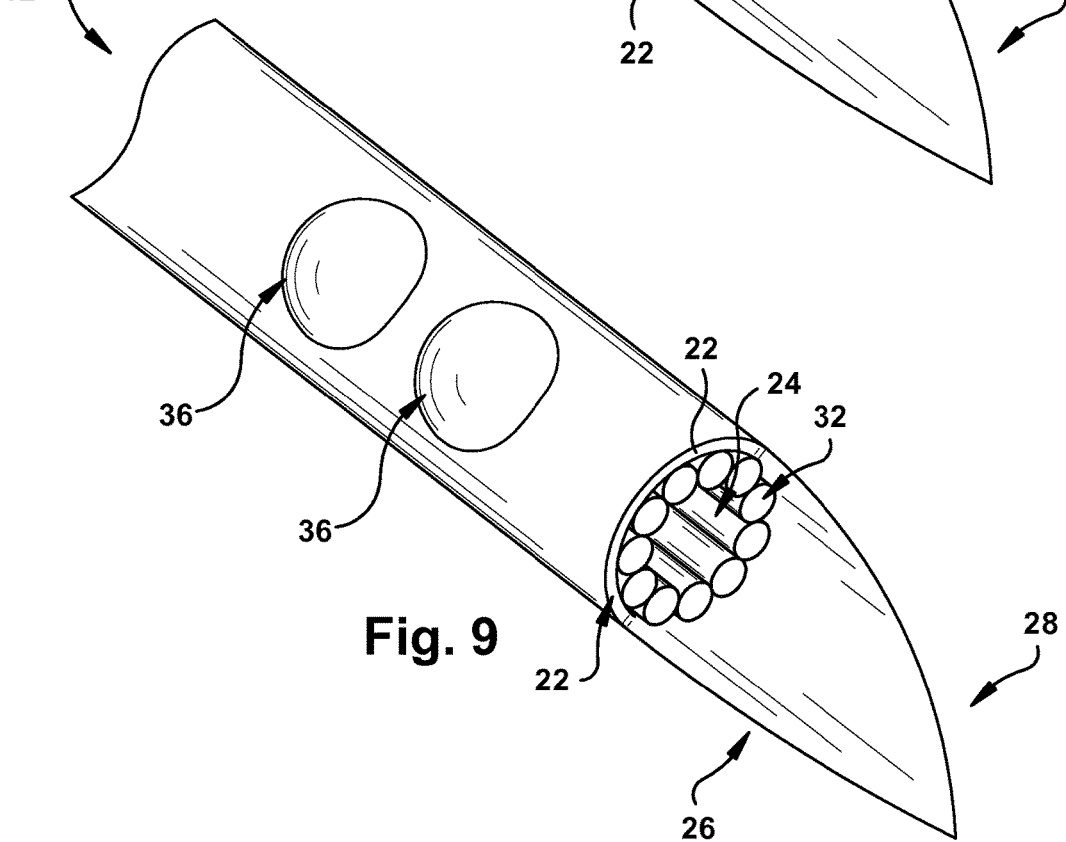

MULTITUBE ESOPHAGEAL BRACHYTHERAPY CATHETER

RELATED APPLICATIONS

This application is a continuation-in-part of U.S. patent application Ser. No. 14/198,793 filed on 6 Mar. 2014, which claims priority to U.S. Provisional Application No. 61/777,671, filed 12 Mar. 2013. The subject matter of all applications is incorporated herein by reference in their entirety.

TECHNICAL FIELD

The present invention relates to an apparatus that includes a delivery system for radiation treatments and, more particularly, to a radiation delivery system for use with brachytherapy.

BACKGROUND OF THE INVENTION

During a radiation treatment session, it may be helpful for a medical professional to fine-tune the exposure of a tumor to supplied radiation. An example of such a radiation treatment session may be a brachytherapy radiation treatment session, whereby a catheter is inserted into a patient's esophagus so that radiation may be supplied to a tumor via an exit port of the catheter.

However, such known brachytherapy catheters may have disadvantages. For example, the catheter may be configured to deliver only a small amount of radiation to the tumor. Thus, it may be desirable, in certain use environments, to deliver an increased quantity of radiation to the tumor. In another example, the catheter may be difficult to pass through the esophagus to the tumor, or the catheter may be difficult to position as desired adjacent the tumor. Thus, a catheter that may be extended through an esophagus and positioned adjacent to a tumor may be desirable.

SUMMARY OF THE INVENTION

In an embodiment of the present invention, a system for delivery of radiation to a target portion of a native tissue is provided during a brachytherapy treatment session. The brachytherapy system includes a catheter that has a main catheter body. The main catheter body includes an outer catheter surface and an inner catheter surface that defines a longitudinally oriented lumen. The lumen extends between longitudinally spaced proximal and distal catheter face surfaces that extend laterally between the inner and outer catheter surfaces. A sheath covers at least a portion of the outer catheter surface. The sheath includes a tapered portion that protrudes substantially longitudinally distally from a portion of the distal catheter face surface. A plurality of tubes extends through the lumen towards the distal catheter face surface. Each tube of the plurality of tubes is configured to selectively guide exposure of a radiation source to the target portion of the native tissue.

In an embodiment of the present invention, a system for selective delivery of radiation to a target portion of a native tissue during a brachytherapy treatment session is provided. The system includes a plurality of tubes connected together in a tube configuration at least partially responsive to a configuration of the target portion of the native tissue. Each tube of the plurality of tubes terminates at a first side of a terminal plane located at a distal end of the plurality of tubes. Each tube of the plurality of tubes is configured to guide exposure of a radiation source to the target portion of the native tissue. At least one plug is configured to fit within at least one tube of the plurality of tubes. The at least one plug is configured to selectively prevent exposure of the radiation source from at least one tube of the plurality of tubes to the target portion of the native tissue.

In an embodiment of the present invention, a method of selectively delivering radiation to a target portion of a native tissue is provided. A delivery system is provided. The delivery system includes a catheter that has a main catheter body. The main catheter body includes an outer catheter surface and an inner catheter surface that defines a longitudinally oriented lumen. The lumen extends between longitudinally spaced proximal and distal catheter face surfaces that extend laterally between the inner and outer catheter surfaces. A sheath covers at least a portion of the outer catheter surface. The sheath includes a tapered portion that protrudes substantially longitudinally distally from the distal catheter face surface. A plurality of tubes extends through the lumen towards the distal catheter face surface. Each tube of the plurality of tubes is configured to selectively guide exposure of a radiation source to the target portion of the native tissue. The delivery system is positioned in a desired position relative to the target portion of the native tissue. A radiation-absorbing plug is inserted into a first chosen amount of tubes of the plurality of tubes to selectively prevent passage of a corresponding radiation source therethrough. A radiation source is inserted into a second chosen amount of tubes of the plurality of tubes. The at least one radiation source is applied to the target portion of the native tissue through the second chosen amount of tubes of the plurality of tubes.

In another embodiment, a system for delivery of radiation to a target portion of a native tissue is provided. The system includes a catheter comprising a catheter body having a proximal portion, a distal portion, and a longitudinally oriented lumen extending between the proximal and distal portions. The system further includes an expansion device disposed about at least a portion of the catheter body and having an expanded configuration and a non-expanded configuration. The system also includes a plurality of tubes disposed about at least a portion of the expansion device, each of the plurality of tubes being configured to selectively guide exposure of a radiation source to the target portion of the native tissue.

In another embodiment, a method of selectively delivering radiation to a target portion of a native tissue is provided. The method comprises inserting a radiation delivery system into a patient's native tissue. The radiation delivery system comprises a catheter comprising a catheter body having a proximal portion, a distal portion comprising a tapered tip with a closed distal end, and a longitudinally oriented lumen extending between the proximal and distal portions. The delivery system further includes an expansion device disposed about at least a portion of the catheter body and having an expanded configuration and a non-expanded configuration. The system also includes a plurality of tubes disposed about at least a portion of the expansion device, each of the plurality of tubes being configured to selectively guide exposure of a radiation source to the target portion of the native tissue. The method further includes inflating an anchor balloon at the native tissue or the target portion of the native tissue. The method also includes adjusting the radial position of the plurality of tubes by expanding the expansion device to radially move the plurality of tubes in closer proximity to the native tissue or the target portion of the native tissue. The method also includes applying radiation to the target portion of the native tissue.

In another embodiment, a method of selectively delivering radiation to a target portion of a native tissue is provided. The method comprises inserting a radiation delivery system into a patient's native tissue. The radiation delivery system includes a catheter comprising a catheter body having a proximal portion, a distal portion, and a longitudinally oriented lumen extending therebetween, the distal portion comprising a tapered tip having a distal opening longitudinally aligned and in fluid communication with the longitudinally oriented lumen of the catheter body. The delivery system further includes an expansion device disposed about at least a portion of the catheter body and having an expanded configuration and a non-expanded configuration. The delivery system further includes a plurality of tubes disposed external to the expansion device, each of the plurality of tubes being configured to selectively guide exposure of a radiation source to the target portion of the native tissue. The method also includes inserting an anchor balloon through the longitudinally oriented lumen and distal opening of the tapered tip. The method further includes adjusting the radial position of the plurality of tubes by expanding the expansion device to radially move the plurality of tubes in closer proximity to the native tissue or the target portion of the native tissue. The method also includes applying radiation to the target portion of the native tissue.

BRIEF DESCRIPTION OF THE DRAWINGS

For a better understanding of the invention, reference may be made to the accompanying drawings, in which:

FIG. 1 is a first side perspective view of an embodiment of the present invention;

FIG. 2 is a schematic side view of the embodiment of FIG. 1;

FIGS. 8 and 9 are side perspective views of the embodiment of FIG. 1 having various configurations;

DESCRIPTION OF EMBODIMENTS

Figure 3:
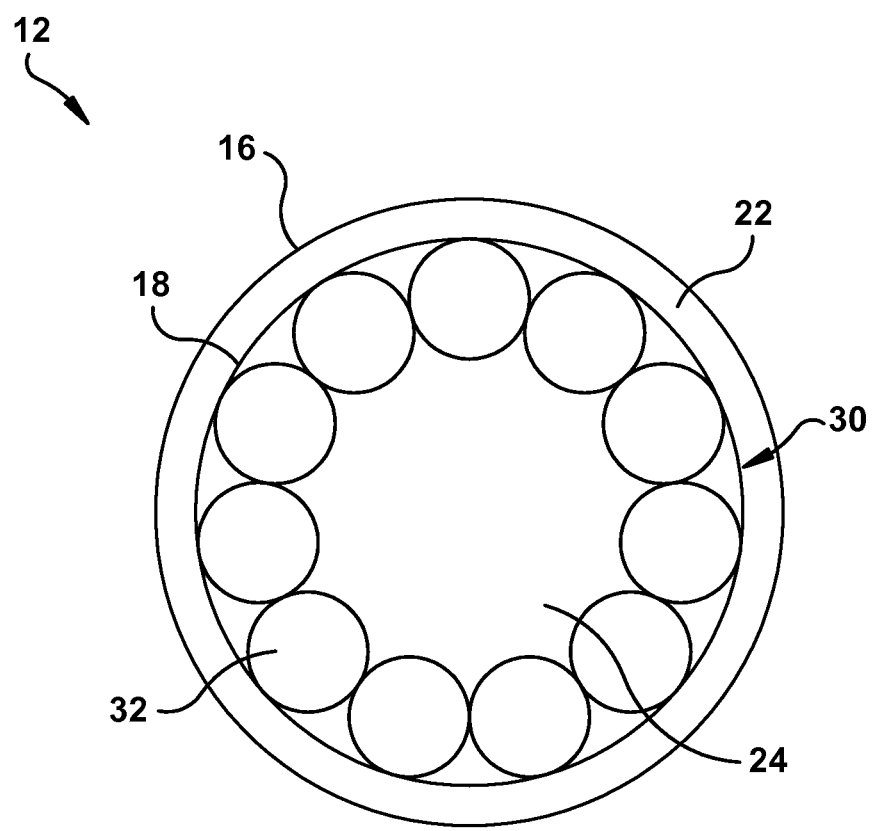
FIG. 3 is a front view of the embodiment of FIG. 1.

The following description presumes that the systems and methods described are being used in conjunction with brachytherapy, but the systems and methods described may be used similarly in any desired manner and for desired purpose without harm to the present invention.

In accordance with an embodiment of the present invention, FIGS. 1-9 depict a delivery system 10. The delivery system 10 may be used for the delivery of at least one radiation source to a target portion of a native tissue. As used herein, the term "native tissue" (and variants thereof) refers to a portion of the patient's body that is of interest, in its condition (congenital or acquired) at the time of surgical preparation. As used herein, the term "target portion" of a native tissue (and variants thereof) refers to a portion of the native tissue (e.g., a tumor, a lesion, etc.) that may be treated using the delivery system 10. However, it will be appreciated that the delivery system 10 may be used with any desired portion of any native tissue of the patient (e.g., esophagus, trachea, stomach, small intestine, large intestine, etc.) for any desired reason or purpose.

As shown in FIG. 1, the delivery system 10 includes a catheter 12 with a main catheter body 14. The main catheter body 14 may be generally circular (or have any other desired cross-sectional shape), and may extend concentrically about a longitudinal axis A. The main catheter body 14 has a length which may be, for example, up to, and including, approximately 1.5 m, and a cross-sectional area which may be, for example, up to, and including, approximately 13 mm for certain uses of the present invention. The main catheter body 14 may be made of a hard plastic (e.g., polyurethane, etc.), a soft plastic (e.g., polyethylene, polypropylene, polyvinyl chloride, etc.), a radioactive material (e.g., technetium-99m, iodine, etc.), or any other suitable material or a combination of materials. The main catheter body 14 shown in FIG. 1 has a semi-rigid configuration or a flexible configuration to assist with navigational efficiency of the delivery system 10 through the patient's body.

The main catheter body 14 includes an outer catheter surface 16 and an inner catheter surface 18. The main catheter body 14 also includes a proximal catheter face surface 20 longitudinally spaced from a distal catheter face surface 22 along the longitudinal axis A. The proximal and distal catheter face surfaces 20 and 22 extend laterally between the outer and inner catheter surfaces 16 and 18. As used herein, the term "laterally" (and variants thereof) refers to a direction substantially located within or along a lateral plane which is substantially cross-sectionally perpendicular to the longitudinal axis A. The inner catheter surface 18 defines a longitudinally oriented lumen 24. The lumen 24 extends between the proximal and distal catheter face surfaces 20 and 22. A guidewire (not shown) may be inserted through the lumen 24 to help guide the delivery system 10 during navigation through the patient's body.

A sheath 26 may be attached to at least a portion of the main catheter body 14. For example, the sheath may be affixed to the main catheter body 14. However, it will be appreciated that the sheath 26 may also or instead be detachable from the main catheter body 14. The sheath 26 covers at least a portion of the distal catheter face surface 22. For example, the sheath 26 may be installed onto the main catheter body 14 so that a portion of the sheath extends distally from the distal catheter face surface 22. It will be appreciated that the sheath 26 may be attached, permanently or temporarily, to any suitable portion of the main catheter body 14 (e.g., the entire outer catheter surface 16, a region of the main catheter body near the distal catheter face surface 22, etc.). The sheath 26 may be made of a soft plastic (e.g., polyethylene, polypropylene, polyvinyl chloride, etc.), or any other suitable material or a combination of materials.

The sheath 26 includes a tapered portion 28 that protrudes substantially longitudinally distally from a portion of the distal catheter face surface 22. It will be appreciated that the tapered portion 28 may have any suitable configuration (e.g., a substantially flat configuration). In one example, the tapered portion 28 may be integrally formed with the sheath 26. In another example, the tapered portion 28 may be attached to the sheath 26 by any suitable method (e.g., welding, adhesives, encircling band, etc.). As shown in FIG. 2, the tapered portion 28 may be configured as a flap-like portion. However, it will be appreciated that the tapered portion 28 may have any suitable configuration (e.g., a spike, a ramp, etc.). The tapered portion 28 may have a semi-rigid configuration or a flexible configuration, as desired, to help guide the delivery system 10 through the native tissue. For example, as shown in FIG. 1, the tapered portion 28 is generally coaxial with the longitudinal axis A. However, as shown in FIG. 2, the tapered portion 28 may be temporarily or permanently deflected upwards or downwards relative to the longitudinal axis A, as described in more detail below.

The tapered portion 28 may be generally made of the same material as the sheath 26. However, it will be appreciated that the tapered portion 28 may be made of any other suitable material or a combination of materials to allow the tapered portion to be deflected in a direction upwards or downwards relative to the longitudinal axis A. Regardless of the material comprising the tapered portion 28, the tapered portion is configured to temporarily or permanently maintain a deflected position relative to the longitudinal axis A to allow the delivery system 10 to navigate through the patient's body, such deflection being facilitated by the tapered portion being at least partially pliable based on the material comprising the tapered portion. In one example, a user may deflect the tapered portion 28 into a desired position, which is maintained relative to the longitudinal axis A, before the delivery system 10 is inserted into the patient's body. In another example, the tapered portion 28 may be deflected relative to the longitudinal axis A upon contact with a portion of the patient's body (e.g., a particularly bulky portion of the native tissue). It will be appreciated that the tapered portion 28 may maintain its deflected position until an applied force (e.g., by the user or a portion of the patient's body) acts upon the tapered portion to adjust the tapered portion into another deflected position. For example, the tapered portion 28 may be further deflected relative to the longitudinal axis A, or the tapered portion may be manipulated back into its original, substantially parallel relationship with the longitudinal axis.

The delivery system 10 is configured to deliver a desired quantity of radiation, described herein as being provided in discrete radiation sources, to the target portion of the native tissue. The delivery system 10 may include a plurality of tubes 30 that includes multiple individual tubes 32. Each tube 32 may be configured to provide a radiation source for delivery to the target portion of the native tissue, as described in more detail below. The tubes 32 are positioned relative to each other in a tube configuration at least partially responsive to a configuration of the target portion of the native tissue. In some use environments, the number of tubes 32 in the plurality of tubes 30 ranges from seven tubes to eleven tubes. In other use environments, the plurality of tubes 30 includes nine tubes 32.

For use as described herein, each tube 32 may have a generally circular cross-sectional shape, and may be made of a hard plastic (e.g., polyurethane, etc.), a soft plastic (e.g., polyethylene, polypropylene, polyvinyl chloride, etc.), or any other suitable material or a combination of materials. Each tube 32 may have a length which can be, for example, up to, and including, approximately 1.5 m, and a cross-sectional area which can be, for example, up to, and including, approximately 3 mm for certain uses of the present invention. The tubes 32 have a semi-rigid configuration or a flexible configuration, as desired, to deliver radiation to the target portion. Some or all of the tubes 32 may be attached to one another in a known manner (e.g., welding, adhesives, encircling band, etc.) sufficient to maintain the relative positions of the tubes to one another during use.

The plurality of tubes 30 extend through the lumen 24 from the proximal catheter face surface 20 to the distal catheter face surface 22. In one example, the plurality of tubes 30 is arranged about a circumference of the inner catheter surface 18. The plurality of tubes 30 may be urged against the inner catheter surface 18, as shown in FIG. 1, in a friction-fit configuration. In another example, the plurality of tubes 30 may be spaced from the inner catheter surface 18, and may be attached to the inner catheter surface by any suitable mechanism (not shown) (e.g., cables, rods, etc.). The plurality of tubes 30 may have a substantially circular arrangement about the longitudinal axis A when viewed from the distal catheter face surface 22. In one example, the plurality of tubes 30 may abut the distal catheter face surface 22. In another example, the plurality of tubes may be spaced from the distal catheter face surface 22. As shown in FIG. 3, each tube 32 of the plurality of tubes 30 longitudinally terminates at the distal catheter face surface 22 such that none of the tubes extend distally from the distal catheter face surface. Each tube 32 of the plurality of tubes 30 is configured to selectively guide exposure of a radiation source to the target portion of the native tissue as desired, as described in more detail below.

Figure 4:
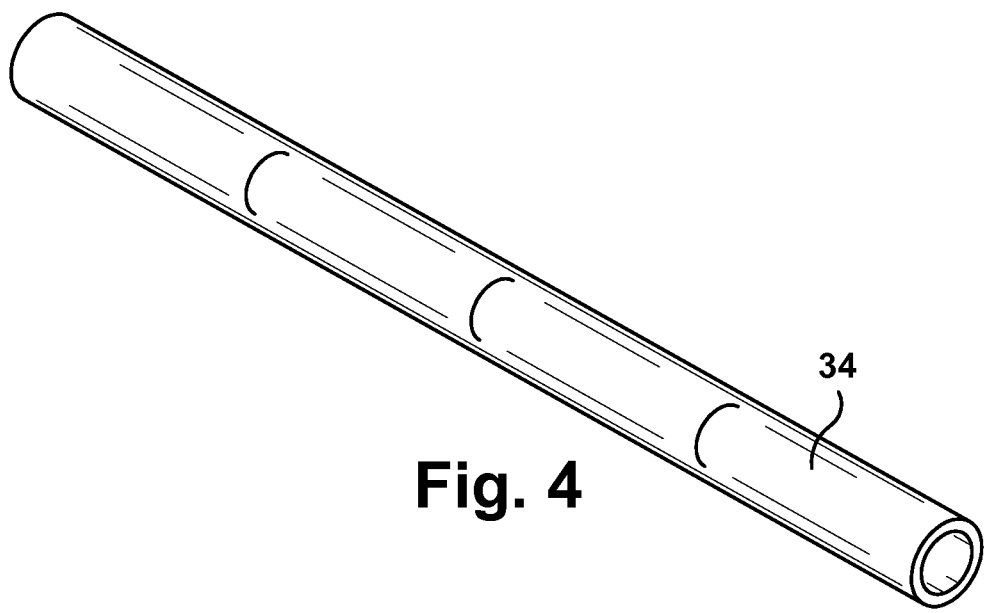
FIG. 4 is a second side perspective view of a portion of the embodiment of FIG. 1.
Figure 5:
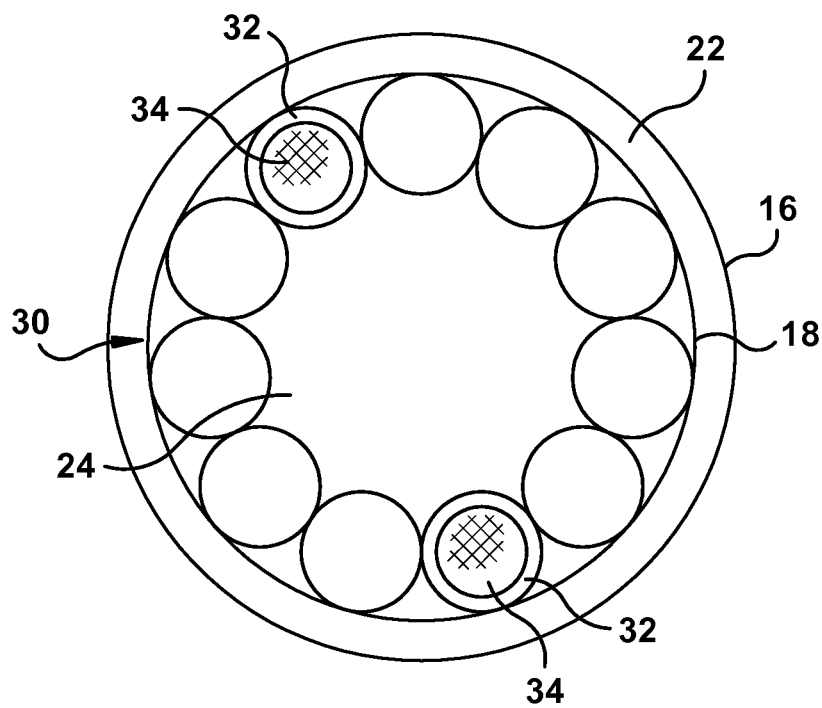
FIG. 5 is a front view of the embodiment of FIG. 1.

As shown in FIGS. 4 and 5, the delivery system 10 may include at least one plug 34 that is sized and dimensioned to fit tightly within one or more chosen tubes 32 of the plurality of tubes 30. The plugs 34 may have a length which can be, for example, up to, and including, approximately 1.5 m, and a cross-sectional area which can be, for example, up to, and including, approximately 2.5 mm. It will be appreciated that the plugs 34 may have sizes and dimensions slightly less than the sizes and dimensions of the corresponding tubes 32 to allow the plugs to snugly fit within the tubes and prevent the plugs from unwanted movement within the tubes. The plugs 34 may have a friction-fit with the tubes 32, the plugs may be installed within the tubes with an adhesive (e.g., glue, putty, etc.), or any other suitable means may be provided to retain the plugs within the tubes (e.g., a seal or gate over the tube openings). The plugs 34 may have a completely rigid configuration, a semi-rigid configuration, or a flexible configuration to allow the plugs to be inserted easily into the tubes 32. The plugs 34 may have a generally circular cross-sectional shape, as shown; however, it will be appreciated that the plugs may have any shape that may be selected, for example, responsive to the internal configuration of the tubes 32. The plugs 34 may be at least partially made of a radiation-absorbing material (e.g., lead, barium sulfate, etc.). The plugs 34 may selectively prevent passage of radiation from the corresponding one or more chosen tubes 32 to the target portion of the native tissue.

Figure 6:
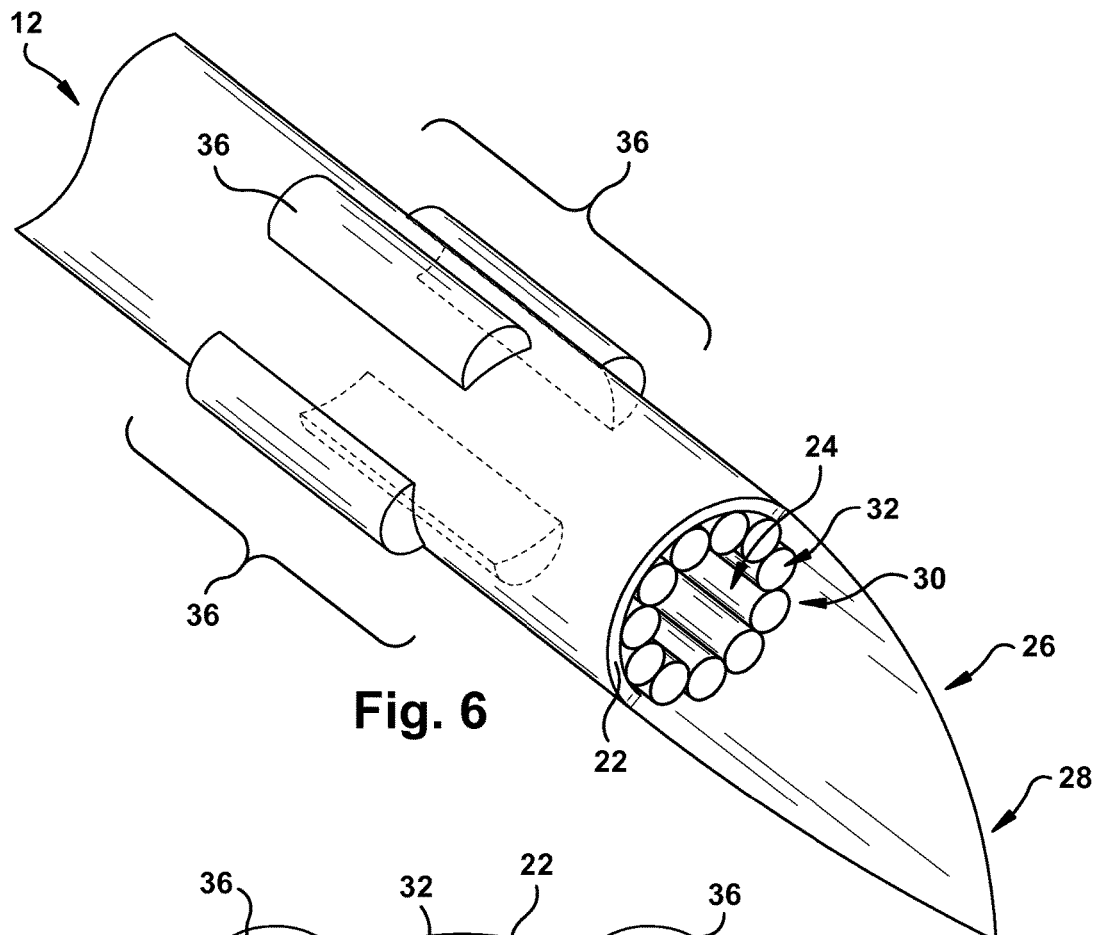
FIG. 6 is a third side perspective view of the embodiment of FIG. 1.
Figure 7:
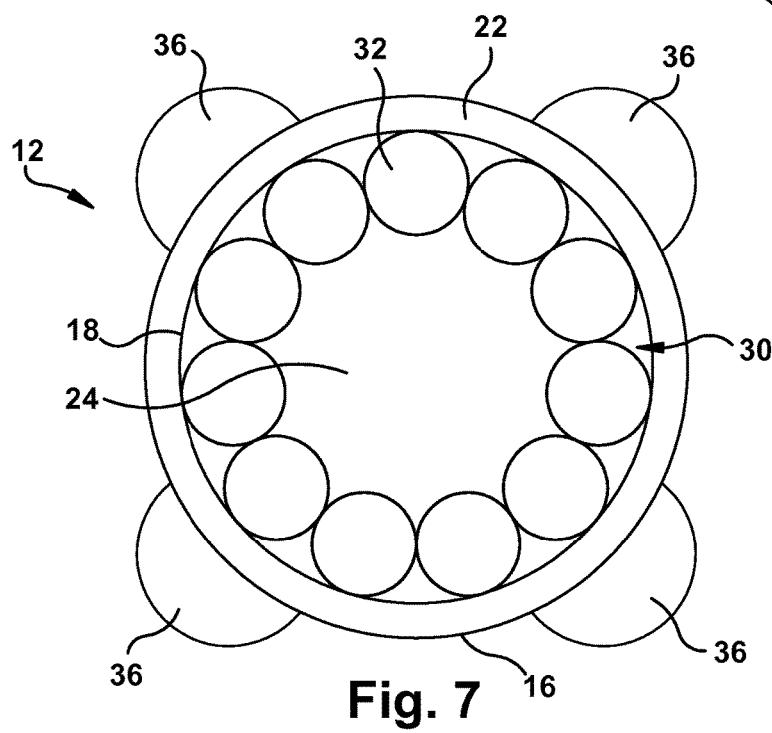
FIG. 7 is a front view of the embodiment of FIG. 1.

As depicted in FIGS. 6-9, the delivery system 10 may further include at least one arrangement mechanism 36 affixed to a portion of the main catheter body 14. FIGS. 6 and 7 show that the arrangement mechanisms 36 may be disposed about at least a portion of the outer catheter surface 16. As depicted in FIGS. 6 and 7, the arrangement mechanisms 36 may be affixed to a portion of the sheath 26 that overlies the outer catheter surface 16. It will be appreciated that the arrangement mechanisms 36 may be located on any other suitable portion of the main catheter body 14 (e.g., the inner catheter surface 18). The arrangement mechanisms 36, when present, may help position and anchor the delivery system 10 by bracing against a portion of the native tissue.

FIGS. 8 and 9 depict the arrangement mechanisms 36 configured as one or more selectively inflatable balloons. It will be appreciated that the arrangement mechanisms 36 may be configured as any suitable mechanism (e.g., rods, plates, etc.) to position the delivery system 10 relative to the native tissue, and/or anchor the delivery system against a portion of the native tissue, as desired. In one example, shown in FIG. 8, the delivery system 10 includes a single arrangement mechanism 36 that anchors and/or positions the delivery system relative to the native tissue. In this instance, the single arrangement mechanism 36 is circumferential about the outer catheter surface 16, similar to a catheter balloon. In another example, shown in FIG. 9, the delivery system 10 includes multiple arrangement mechanisms 36 that anchor and/or position the delivery system relative to the native tissue. In this instance, the multiple arrangement mechanisms 36 are arranged in a spaced-apart relation to one another on a portion of the outer catheter surface 16. The multiple arrangement mechanisms 36 may be arranged in any longitudinal or lateral configuration (e.g., offset, spaced from each other, adjacent, etc.) with respect to the main catheter body 14 to position the delivery system 10 as desired relative to the native tissue. The arrangement mechanisms 36 may be selectively inflated to contact the native tissue for anchoring and/or positioning the delivery system 10 relative to the native tissue, as discussed in more detail below.

Figure 10:
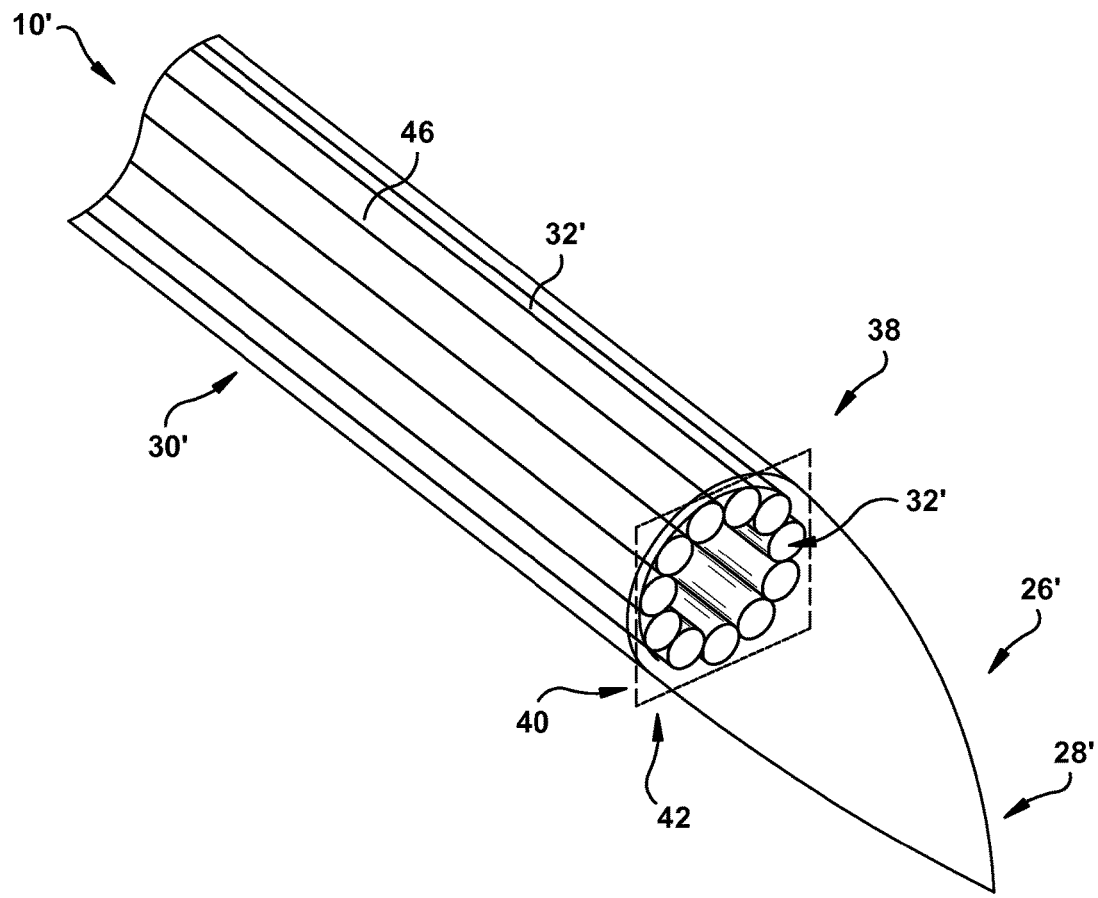
FIG. 10 is a side perspective view of an embodiment of the present invention.
Figure 11:
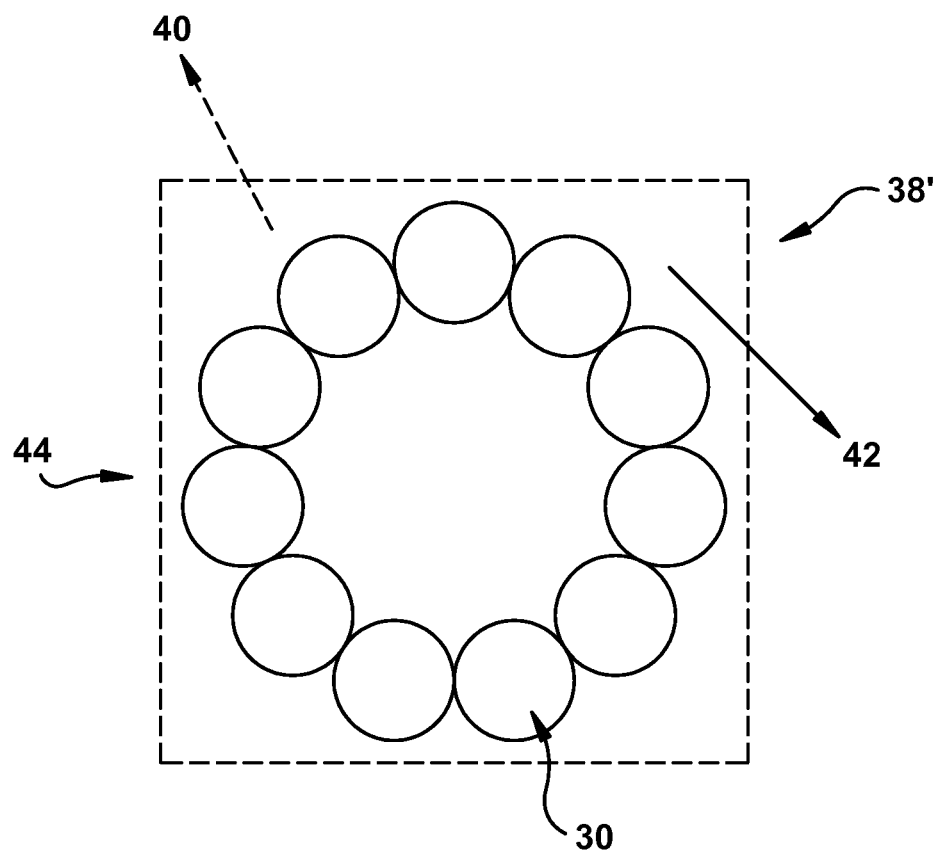
FIG. 11 is a front view of the embodiment of FIG. 10.
Figure 12:
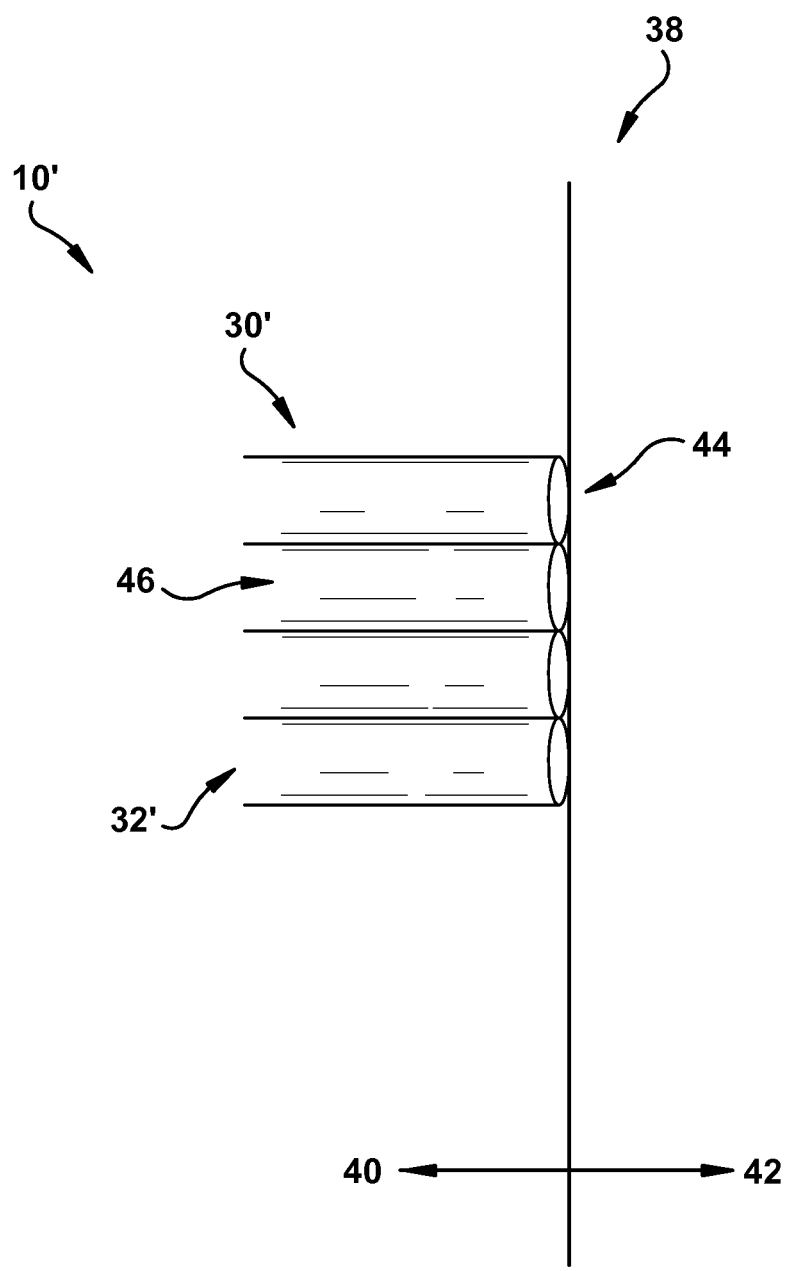
FIG. 12 is a side view of the embodiment of FIG. 10.

FIGS. 10-12 illustrate another embodiment of the delivery system 10. The delivery system 10' of FIGS. 10-12 is similar to the delivery system of FIGS. 1-9 and, therefore, structures of FIGS. 10-12 that are the same as, or similar to, those described with reference to FIGS. 1-9 have the same reference numbers with the addition of a "prime" mark. Description of common elements and operation similar to those in the previously described embodiment will not be repeated with respect to the currently described embodiment.

The delivery system 10' includes a plurality of tubes 30' with multiple individual tubes 32', but without the catheter 12 of the delivery system 10. In one example, the number of tubes 32' in the plurality of tubes 30' may range from seven tubes to eleven tubes. In another example, the delivery system 10' includes nine tubes 32'. Each tube 32' of the plurality of tubes 30' is disposed at a terminal plane 38 that defines a proximal plane side 40 and a distal plane side 42. Each tube 32' of the plurality of tubes 30' longitudinally terminates at the proximal plane side 40 such that each tube 32' does not substantially extend into the distal plane side 42, as shown in FIGS. 11 and 12.

As shown in FIG. 10, the delivery system 10' includes a portion of the sheath 26'.

The sheath 26' is affixed to a collective distal end 44 of each tube 32' of the plurality of tubes 30' substantially disposed on the proximal plane side 40 of the terminal plane 38. It will be appreciated that the collective distal end 44 of the tubes 32' may generally correspond to the proximal plane side 40. In this use environment, the tapered portion 28' of the sheath 26' extends from the collective distal end 44 of the plurality of tubes 30', through the terminal plane 38, and into the distal plane side 42.

Figure 13:
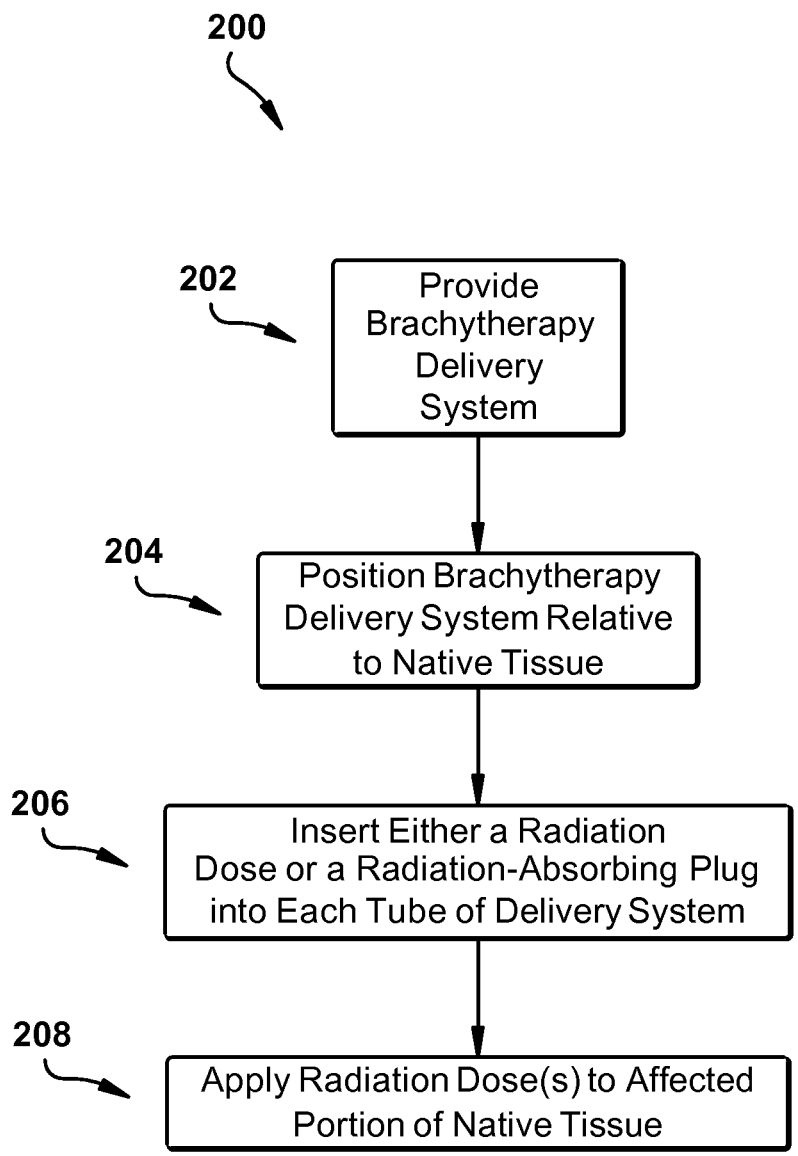
FIG. 13 is a flow chart illustrating an example process for using an embodiment of the present invention.

FIG. 13 shows a flow chart 200 representing a sequence of use of the delivery systems 10 and 10' during a brachy-therapy treatment session. In a first action block 202 of the flow chart 200, the delivery system 10, as described above, is provided.

Figure 14:
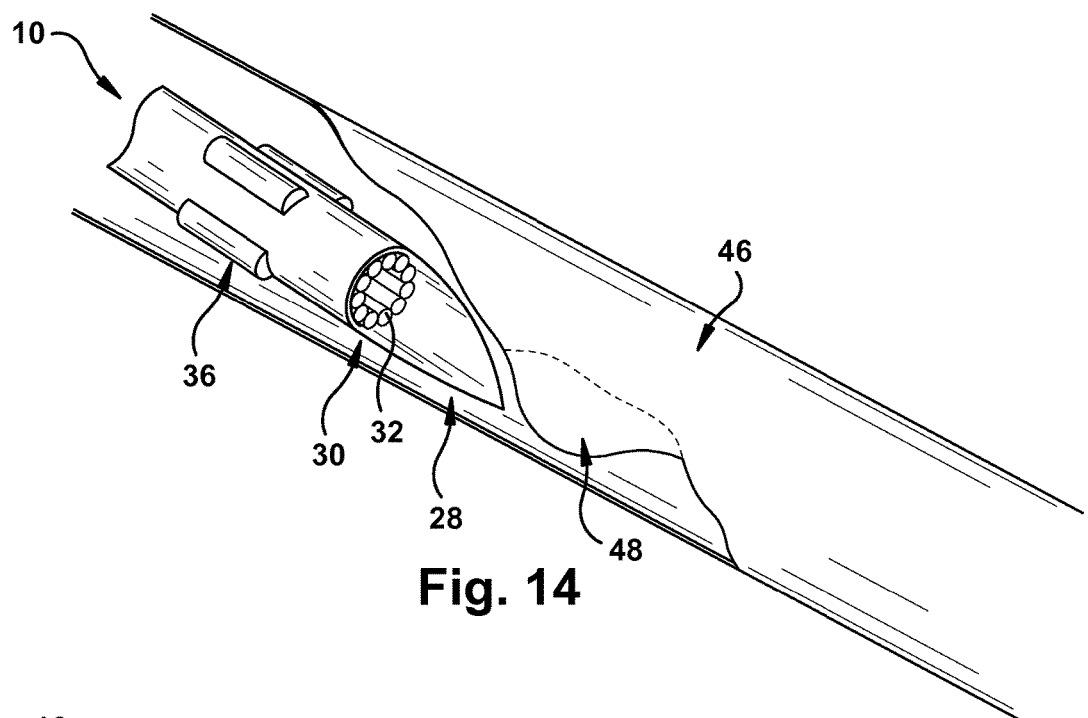
FIGS. 14-17 are perspective views depicting a sequence of operation of the present invention.

In a second action block 204 of the flow chart 200, the delivery system 10 is positioned relative to a native tissue 46. As shown in FIG. 14, the delivery system 10 is inserted into a portion of the native tissue 46 near a target portion 48 thereof. In one example, the delivery system 10 is positioned such that the plurality of tubes 30 is approximately adjacent to at least an outer contour of the target portion 48. In another example, the delivery system 10 is positioned such that the plurality of tubes 30 contacts at least the outer contour of the target portion 48.

Figure 15:
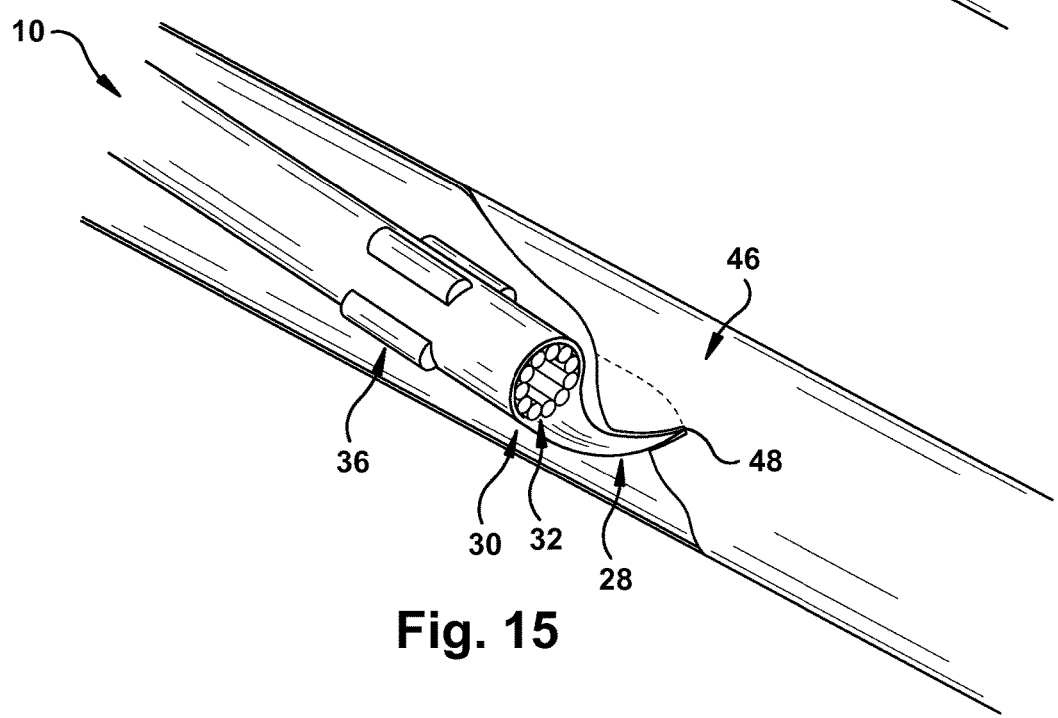

The tapered portion 28 of the sheath 26 may include a semi-rigid configuration or a flexible configuration to act as a guide for helping navigation of the delivery system 10 through the native tissue 46. The tapered portion 28 may be made of a suitably pliable material to allow the tapered portion to be deflected upwards or downwards relative to the longitudinal axis A. In one example, a user may deflect the tapered portion upwards or downwards relative to the longitudinal axis A into a desired position relative to the longitudinal axis before the delivery system 10 is inserted into the patient's body. The deflected position of the tapered portion 28 may assist in navigation of the delivery system 10 through the native tissue 46. Additionally, the deflected position of the tapered portion 28 may also assist with placement of the plurality of tubes 30 in a desired position relative to the target portion 48 (e.g., adjacent to the target portion, contacting the target portion, etc.). In another example, the tapered portion 28 may be sized and dimensioned to provide leverage to create clearance for the delivery system 10 to extend past, e.g., a particularly bulky portion of the native tissue 46. In a further example, the tapered portion 28 may be deflected relative to the longitudinal axis A upon contact with a portion of the patient's body (e.g., a particularly bulky portion of the native tissue). Regardless of the manner in which the tapered portion is deflected, the now-deflected tapered portion 28 may allow the delivery system 10 to "cup" the target portion 48, as shown in FIG. 15, thereby increasing the surface area of the target portion that is contacted by the plurality of tubes 30.

Once the tapered portion 28 has been deflected, it will be appreciated that the tapered portion may maintain its deflected position until another force (e.g., the user or a portion of the patient's body) acts upon the tapered portion to deflect the tapered portion into another deflected position. For example, the tapered portion 28 may be further deflected relative to the longitudinal axis A, or the tapered portion can be manipulated back into a non-deflected, coaxial relationship with the longitudinal axis. In another example, the tapered portion 28 may be at least partially comprised of a shape memory material (e.g., nitinol, etc.) to allow the tapered portion to return to the non-deflected original position. In a further example, the tapered portion can include a spring-biased or other movement mechanism (not shown) to deflect the tapered position into the non-deflected position or another deflected position.

Figure 16:
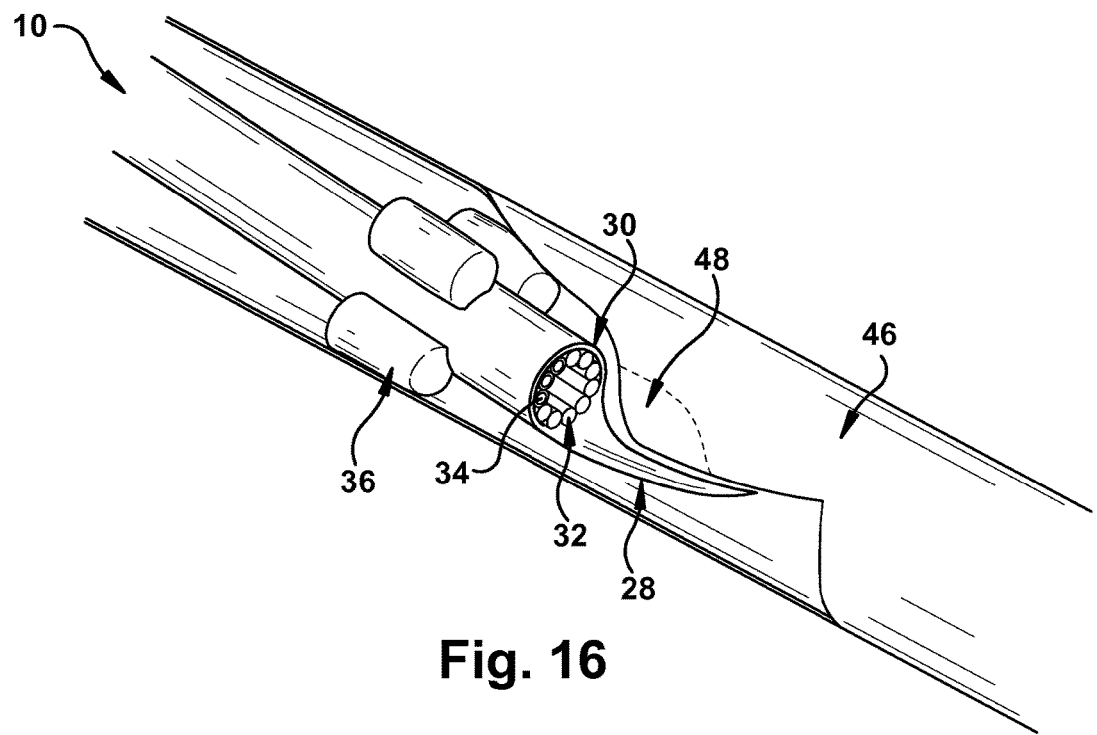

The delivery system 10 may be anchored, at any desired time in the use process, to the native tissue 46 relative to the target portion 48. The arrangement mechanisms 36 may be selectively inflated to anchor and position the delivery system 10 relative to the target portion 48. As shown in FIG. 16, the arrangement mechanisms 36 may be inflated to contact portions (e.g., tangential surfaces) of the surrounding native tissue 46. The arrangement mechanisms 36 may be inflated to a desired amount until the delivery system 10 is urged against the native tissue 46, thereby anchoring and positioning the delivery system relative to the target portion 48. For example, multiple arrangement mechanisms 36 can be inflated to different degrees relative to each other to allow for an off-center, or any other desired, placement of the delivery system 10 against the native tissue 46.

Once the delivery system 10 is positioned and anchored in a desired position relative to the target portion 48, at least one radiation source may be exposed to the target portion. In a third action block 206 of the flow chart 200, a radiation source may be individually inserted into a chosen amount of tubes 32. The radiation source may be any suitable form of radiation-providing material (e.g., a solid rod, a seed-like structure containing a radioactive material, a fluid, etc.). In one example, a radiation source may be inserted into each tube 32. In another example, a radiation source may be inserted into a first chosen number (e.g., less than seven) of tubes 32.

In some use environments, it may be desirable to protect a "healthy" (e.g., non-target) portion of the native tissue 46 from exposure to radiation passing through the tubes 32 to the target portion. To prevent such unwanted exposure, one or more plugs 34 may be inserted into a second chosen number of tubes 32 (e.g., the remaining ones of the plurality of tubes 30 not included in the first chosen number of tubes). It will be appreciated that the plugs 34 may be inserted into the second chosen number of tubes 32 before, during, or after the radiation sources are inserted into the first chosen number of tubes. Since the plugs 34 are at least partially made of a radiation-absorbing material, the plugs may help prevent unwanted radiation exposure to portions of the native tissue 46 other than the target portion 48.

Figure 17:
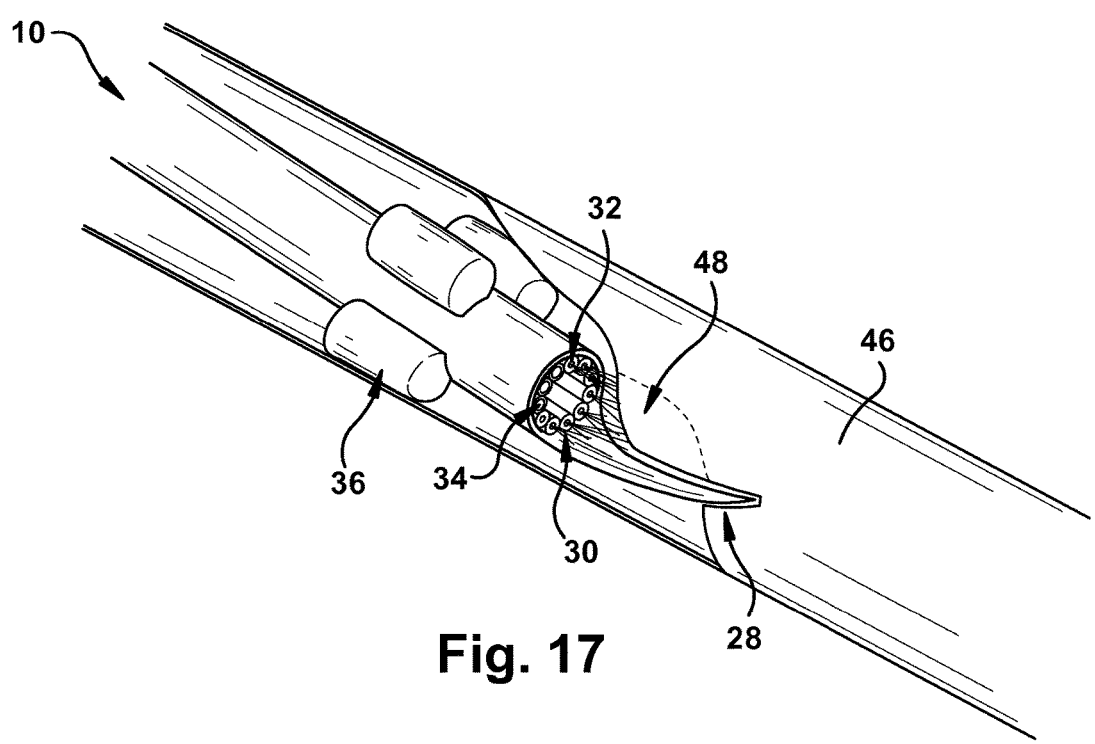

In a fourth action block 208 of the flow chart 200, the radiation sources are delivered to the target portion 48 of the native tissue 46, thereby exposing the target portion to the radiation. In one use environment, the radiation sources are positioned at the proximal catheter face surface 20 to deliver radiation through the length of the chosen number of tubes 32 and out of the distal catheter face surface 22. In this use environment, the radiation sources deliver radiation through the first chosen number of tubes 32, thereby exposing the target portion 48 to the radiation. In another use environment, as shown in FIG. 17, the radiation sources extend through the length of the chosen number of tubes 32 and are positioned at the distal catheter face surface 22 to expose the target portion 48 to the radiation. In either use environment, the radiation sources directly contact the target portion 48, or are otherwise positioned adjacent the target portion, thereby exposing the target portion to the radiation. In any use environment, the plurality of tubes 30 facilitates exposure of the target portion 48 to a desired quantity of radiation. A deflected position of the tapered portion 28 may facilitate positioning of the plurality of tubes 30 in a desired relationship (e.g., relatively closer) to the target portion 48, thereby increasing the exposure of the target portion to radiation.

In other aspects of the present invention, a system for delivery of radiation to a target portion of a native tissue is provided that includes an expansion device. Such an expansion device allows a user to adjust the radial position of the plurality of tubes. For example, such an expansion device allows a user to radially move the plurality of tubes in closer proximity the native tissue or the target portion of the native tissue.

Figure 18:
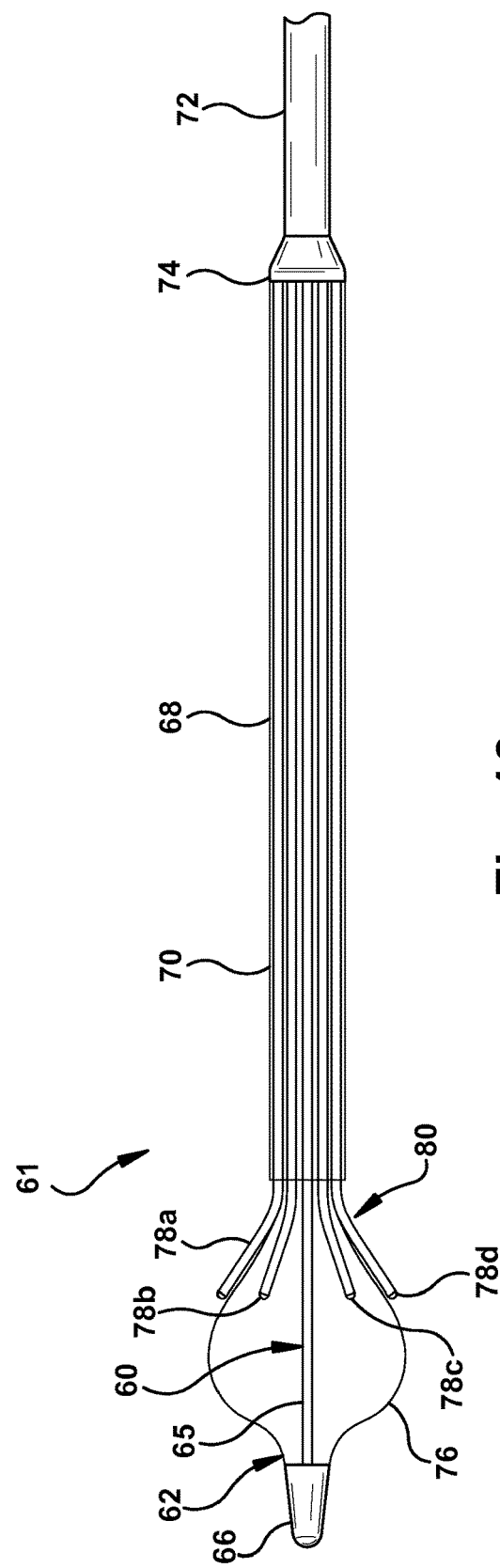
FIG. 18 is a side view of an embodiment of the present invention.
Figure 19:
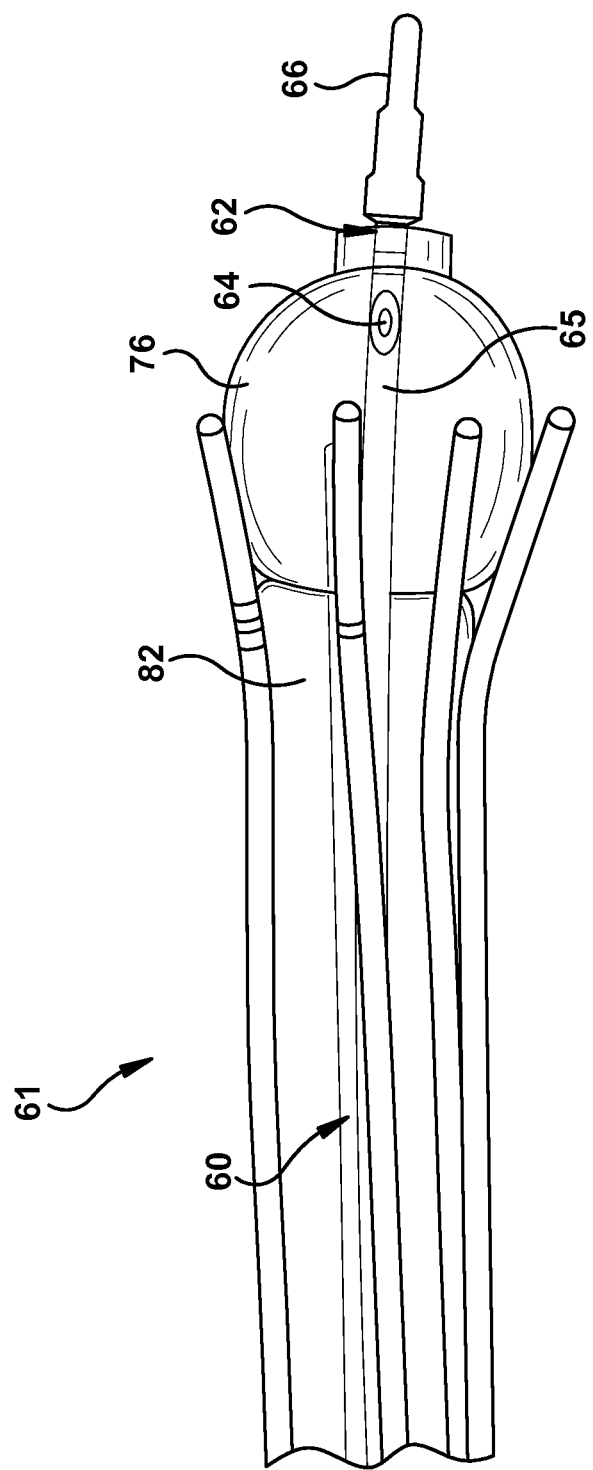
FIG. 19 is a side view of an embodiment of the present invention.

For example, referring to FIG. 18, in certain embodiments, a system 61 includes a catheter 60 comprising a catheter body 65 having a proximal portion (not shown), a distal portion 62, and a longitudinally oriented lumen extending therebetween. Referring to FIG. 19, system 61 can further include an expansion device 82 disposed about at least a portion of catheter body 65. Expansion device 82 can assume an expanded configuration and a non-expanded configuration. As such, expansion device can be fabricated of any suitable material that allows the device to assume such configurations. For example, expansion device can have an outer layer fabricated from silicone rubber and an inner layer fabricated from a nylon elastomer. System 61 can further include a plurality of tubes 78 disposed about at least a portion of expansion device 82. As described above, each of the plurality of tubes 78 are configured to selectively guide exposure of a radiation source to the target portion of the native tissue.

Distal portion 62 of catheter body 65 can have a tapered tip 66 as illustrated in FIGS. 18 and 19. In certain embodiments, the tapered tip has a closed distal end and in other embodiments, the tapered tip has a distal opening longitudinally aligned and in fluid communication with the longitudinally oriented lumen of catheter body 65. The tapered tip can be fabricated from an elastomeric material. Referring to FIG. 19, in certain embodiments, the longitudinally oriented lumen of catheter body 65 has a longitudinal axis and distal portion 62 of catheter body 65 defines a lateral port 64 that is non-concentric with the longitudinal axis. A guidewire can be urged through lateral port 64 and therefore facilitate guidewire navigation. Preferably, lateral port 64 is included in embodiments where the tapered tip of the catheter body has a closed distal end.

Referring to FIG. 18, in certain embodiments, a sheath 68 having a distal portion 70 and a proximal portion 72 is disposed about at least a portion of catheter 60 proximal to distal tip 66. At least portions of sheath 68 may be fabricated from an elastomeric material, which allows it to be introduced and/or retracted in a small diameter state, yet accommodate expandable device 82 and anchor balloon 76 (described below). For example, distal portion 70 of sheath 68 can house expandable device 82 and anchor balloon 76 and therefore be fabricated from an expandable material whereas proximal portion 72 can be fabricated from a non-expandable material. Portions 70 and 72 may be sealed at a seam 74 or otherwise connected and in fluid communication with one another.

Referring to FIGS. 18 and 19, in certain embodiments, an anchor balloon 76 can be disposed about distal portion 62 of catheter body 65 (proximal to distal tip 66 and distal to expandable device 82) and can assume an inflated and deflated configuration. Anchor balloon 76 can be disposed inside of sheath 68 in a deflated configuration and extend outside of sheath 68 in an inflated configuration as shown in FIG. 18. Anchor balloon 76 may be used for several purposes. For example, the anchor balloon can be used to dilate the native tissue, such as the esophagus, for example, when introducing system 61 into a stricture; secure the position of system 61 within the native tissue, such as the esophagus or stomach, for example, at the gastroesophageal junction (GEJ); and/or reposition the plurality of plurality of tubes 78 in closer proximity to a target portion of native tissue, such as a tumor involving the GEJ and proximal gastric cardia.

Referring to FIG. 18, at least a portion of plurality of tubes 78 is disposed inside of sheath 68. The plurality of tubes can be disposed substantially parallel to each other. As shown in FIG. 18, a distal section 80 of the plurality of tubes 78 can be disposed on anchor balloon 76 so that when anchor balloon 76 is inflated, distal section 80 of the plurality of tubes 76 is deflected radially. Such a configuration may be useful when treating the GEJ and proximal gastric cardia.

The plurality of tubes 78 can incorporate fiducial markers visible under various types of imaging.

In certain embodiments, a delivery system further includes a mouth guard disposed at the proximal portion of the catheter that can be placed in the patient's mouth during treatment. Such a mouth guard can have a central opening with a locking mechanism through which a medical instrument can be inserted. Such medical devices include, for example, any of the devices described herein including other transoral devices such as an esophagogastroduodenoscope with or without a guidewire. Such a mouth guard can also serve as a bite block.

Figure 20:
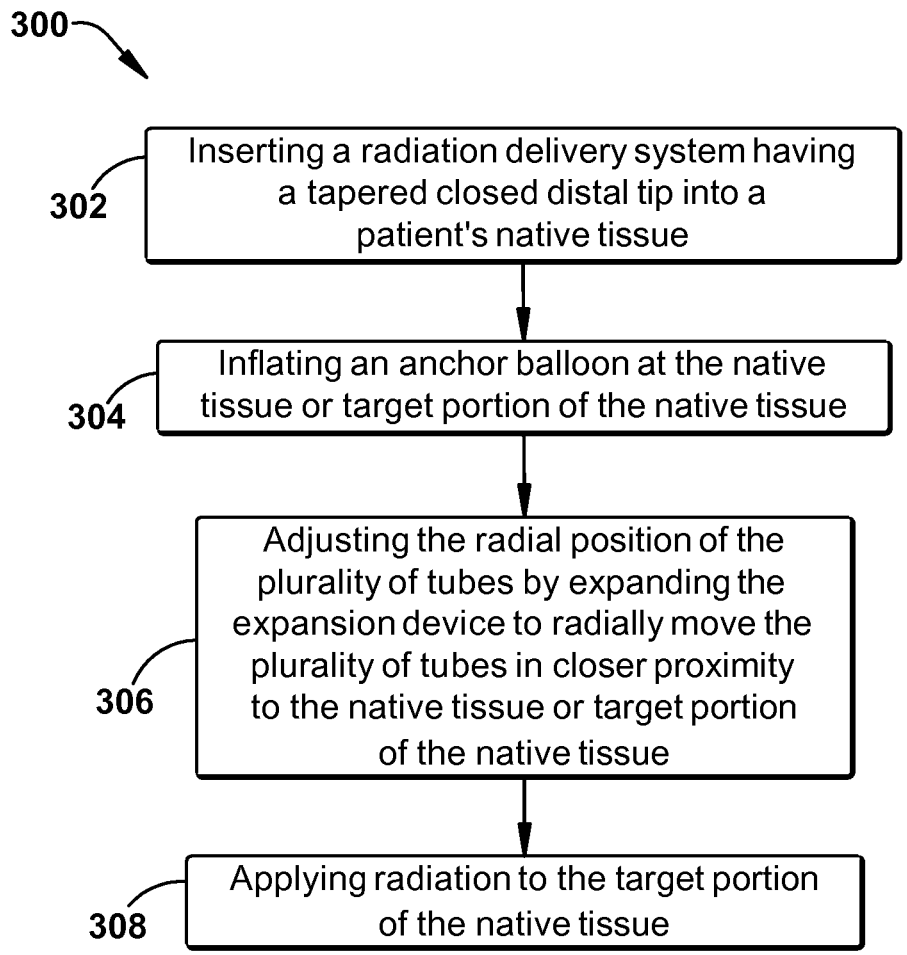
FIG. 20 is a flow chart illustrating an example process for using an embodiment of the present invention.

FIG. 20 shows a flow chart 300 representing a sequence of use of an embodiment of a delivery system 61 having a tapered closed distal tip during a brachytherapy treatment session. In a first action block 302, system 61 can be inserted into a patient's native tissue. In a second action block 304, an anchor balloon 76 can be inflated at the native tissue or the target portion of the native tissue. In a third action block 306, the radial position of the plurality of tubes 78 can be adjusted by expanding the expansion device 82 to radially move the plurality of tubes 78 in closer proximity to the native tissue or the target portion of the native tissue. In a fourth action block 308, radiation can be applied to the target portion of the native tissue.

Regarding a specific exemplary method, a mouth guard mounting unit can be placed in the patient. An esophagogastroduodenoscopy with placement of a guide wire through an EGD scope into the stomach or esophagus can be performed. The guide wire can be inserted through the lateral port of the catheter of system 61, as described above. System 61 can be inserted into the patient's esophagus. Anchor balloon 76 can be inflated to dilate the esophagus or the esophageal tumor, secure catheter 60, or reposition the plurality of tubes 78. If it is desired to treat the GEJ or proximal gastric cardia, anchor balloon 76 can be inflated such that the plurality of tubes 78 is held in contact with the tissue of the GEJ and proximal gastric cardia. The radial position of the plurality of tubes 78 can be adjusted by expanding expansion device 82 to radially move the plurality of tubes 78 in closer proximity to the esophageal wall and/or tumor. Plugs, as described above, can be placed in selected tubes 78 to modulate the radiation dose and decrease the radiation does to uninvolved, normal tissue. CT and/or MRI imaging can be completed with system 61 in position for radiation treatment planning. An optimized radiation treatment plan using forward or inverse planning can be used to deliver the radiation to the target portion of the native tissue. After the treatment is completed, expansion device 82 can be retracted followed by deflation of anchor balloon 76. Delivery system 61 can then be removed from the patient.

Figure 21:
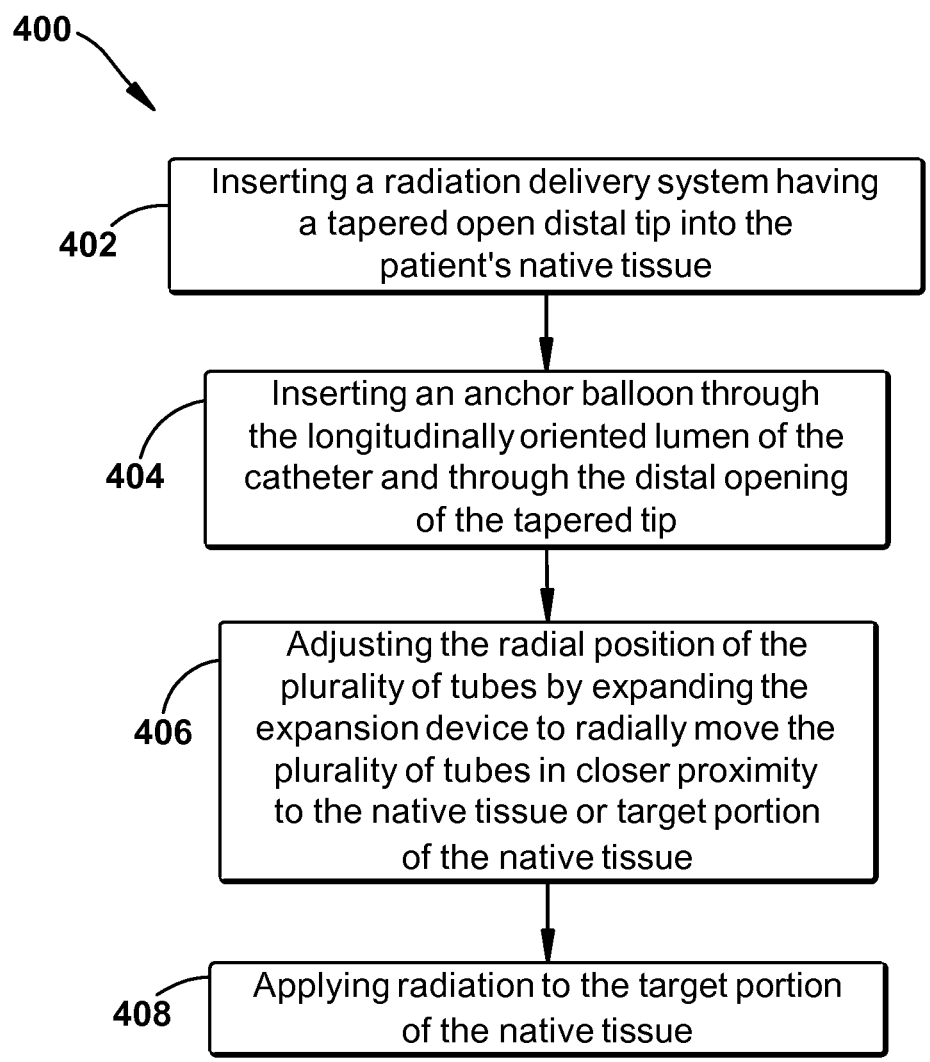
FIG. 21 is a flow chart illustrating an example process for using an embodiment of the present invention.

FIG. 21 shows a flow chart 400 representing a sequence of use of an embodiment of a delivery system 61 having an tapered open distal tip during a brachytherapy treatment session. In a first action block 402, system 61 can be inserted into a patient's native tissue. In a second action block 404, an anchor balloon can be inserted through the longitudinally oriented lumen of catheter 60 and through the distal opening of the tapered tip. In a third action block 406, the radial position of the plurality of tubes 78 can be adjusted by expanding the expansion device 82 to radially move the plurality of tubes 78 in closer proximity to the native tissue or the target portion of the native tissue. In a fourth action block 408, radiation can be applied to the target portion of the native tissue.

Regarding a specific exemplary method, a mouth guard mounting unit can be placed in the patient. An esophagogastroduodenoscopy with placement of a guide wire through an EGD scope into the stomach or esophagus can be performed. A dilating balloon can be delivered through the longitudinally oriented lumen of the catheter 60 of the delivery system and through the distal opening of the tapered tip into the esophagus over a guidewire or together with a guidewire to dilate the esophagus or the esophageal tumor. The dilating balloon can be removed after dilation while the guide wire remains in place in the longitudinally oriented lumen and open tapered tip. Delivery system 61 can be inserted into the patient's esophagus over the guide wire. An anchor balloon can be inserted through the longitudinally oriented lumen of delivery system 61 and through the distal opening of the tapered tip. The position of catheter 60 can be secured by inflating the anchor balloon and/or attaching catheter 60 to the mouth guard mounting unit. The anchor balloon can be inflated in the stomach or another location along the esophagus to secure delivery system 61. Alternatively, to avoid interchanging a dilation balloon and an anchor balloon, the dilating balloon can also serve as the anchor balloon. In other words, the dilating balloon can be inserted through the longitudinally oriented lumen of delivery system 61 and through the distal opening of the tapered tip and inserted together as a unit into the patient's esophagus along the guidewire. To adjust the radial position of the plurality of tubes 76, the expansion device 82 can be expanded to radially move the plurality of tubes in closer proximity to the esophageal wall and/or tumor. Plugs, as described above, can be placed in selected tubes to modulate the radiation dose and decrease the radiation does to uninvolved, normal tissue. CT and/or MRI imaging can be completed with system 61 in position for radiation treatment planning. An optimized radiation treatment plan using forward or inverse planning can be used to deliver the radiation to the target portion of the native tissue. After the treatment is completed, expansion device 82 can be retracted followed by deflation of the anchor balloon. The anchor balloon can be removed through the distal opening of the tapered tip and the longitudinally oriented lumen of catheter 60. Delivery system 61 can then be removed from the patient.

While aspects of the present invention have been particularly shown and described with reference to the preferred embodiment above, it will be understood by those of ordinary skill in the art that various additional embodiments may be contemplated without departing from the spirit and scope of the present invention. For example, the specific methods described above for using the delivery systems are merely illustrative; one of ordinary skill in the art could readily determine any number of tools, sequences of steps, or other means/options for placing the above-described apparatus, or components thereof, into positions substantially similar to those shown and described herein. Any of the described structures and components could be integrally formed as a single unitary or monolithic piece or made up of separate sub-components, with either of these formations involving any suitable stock or bespoke components and/or any suitable material or combinations of materials; however, the chosen material(s) should be biocompatible for many applications of the present invention. Though certain components described herein are shown as having specific geometric shapes, all structures of the present invention may have any suitable shapes, sizes, configurations, relative relationships, cross-sectional areas, or any other physical characteristics as desirable for a particular application of the present invention. Unless otherwise specifically stated, contact could be either direct or indirect. Any structures or features described with reference to one embodiment or configuration of the present invention could be provided, singly or in combination with other structures or features, to any other embodiment or configuration, as it would be impractical to describe each of the embodiments and configurations discussed herein as having all of the options discussed with respect to all of the other embodiments and configurations. A device or method incorporating any of these features should be understood to fall under the scope of the present invention as determined based upon the claims below and any equivalents thereof.

Other aspects, objects, and advantages of the present invention may be obtained from a study of the drawings, the disclosure, and the appended claims.

What is claimed is:

1. A system for delivery of radiation to a target portion of a native tissue, the system comprising:
    a catheter comprising a catheter body having a proximal portion, a distal portion, and a longitudinally oriented lumen therebetween;
    an expansion device disposed about at least a portion of the catheter body and having an expanded configuration and a non-expanded configuration;
    an anchor balloon disposed about the catheter body distal to the expansion device and having an inflated configuration and a deflated configuration, the anchor balloon having a curved outer surface in an inflated configuration;
    a plurality of tubes disposed about at least a portion of the expansion device and disposed only part-way along the longitudinal length of the anchor balloon along the curved outer surface, each of the plurality of tubes being configured to selectively guide exposure of a radiation source to the target portion of the native tissue.

2. The system of claim 1, wherein the distal portion of the catheter body comprises a tapered tip having a closed distal end.

3. The system of claim 2, wherein the longitudinally oriented lumen has a longitudinal axis and the distal portion of the catheter body defines a lateral port non-concentric with the longitudinal axis.

4. The system of claim 1, wherein a distal section of the plurality of tubes is deflected radially when the anchor balloon assumes an inflated configuration.

5. The system of claim 1, further comprising a sheath disposed at least partially about the plurality of tubes.

6. A method of selectively delivering radiation to a target portion of tissue at the gastroesophageal junction comprising:
    inserting a radiation delivery system into a patient's body, the radiation delivery system comprising:
        a catheter comprising a catheter body having a proximal portion, a distal portion and a longitudinally oriented lumen extending therebetween;
        an expansion device disposed about at least a portion of the catheter body;
        an anchor balloon disposed about the catheter body distal to the expansion device, the anchor balloon having a curved outer surface in an inflated configuration;
        a plurality of tubes disposed about at least a portion of the expansion device, each of the plurality of tubes being configured to selectively guide exposure of a radiation source to the target portion of the tissue at the gastroesophageal junction;
    inflating the anchor balloon to position the distal ends of the plurality of tubes in close proximity to the target portion of the tissue at the gastroesophageal junction, the plurality of tubes disposed only part-way along the longitudinal length of the anchor balloon along the curved outer surface;
    adjusting the radial position of the plurality of tubes by expanding the expansion device to radially move the plurality of tubes in closer proximity to the gastroesophageal junction or the target portion of the tissue at the gastroesophageal junction;
    inserting a radiation source into one or more of the plurality of tubes; and
    selectively applying radiation to the target portion of the tissue at the gastroesophageal junction.

7. The method of claim 6, wherein the anchor balloon, in an inflated configuration, dilates the native tissue.

8. The method of claim 6, wherein the anchor balloon, in an inflated configuration secures the position of the catheter within the native tissue.

9. The method of claim 6, wherein the anchor balloon, in an inflated configuration, repositions the plurality of tubes in closer proximity to the target portion of the native tissue.

10. The method of claim 6, further comprising inserting a mouth guard in the patient's mouth prior to inserting the radiation delivery system.

11. The method of claim 6, wherein the target portion of the tissue is a tumor.

12. The method of claim 6, further comprising:
    completing computer tomography (CT) and/or magnetic resonance imaging (MRI) with the radiation delivery system in place for radiation treatment planning; and
    using forward or inverse planning to deliver radiation to the target portion of the tissue.

* * * * *